United States Patent [19]

Waller

[11] 4,063,360
[45] Dec. 20, 1977

[54] ORTHODONTIC BRACKET ASSEMBLY AND METHOD FOR ATTACHMENT

[75] Inventor: Duncan E. Waller, Milford, Del.

[73] Assignee: Dentsply Research & Development Corporation, Milford, Del.

[21] Appl. No.: 464,278

[22] Filed: Apr. 25, 1974

[51] Int. Cl.$^2$ .............................................. A61C 7/00
[52] U.S. Cl. ...................................................... 32/14 A
[58] Field of Search ............................................ 32/14

[56] References Cited
U.S. PATENT DOCUMENTS

| 2,960,803 | 11/1960 | Bonistall | 32/14 A |
| 3,629,187 | 12/1971 | Waller | 260/42.52 |
| 3,638,312 | 2/1972 | Szwarc | 32/15 |
| 3,765,091 | 10/1973 | Northcutt | 32/14 A |
| 3,932,940 | 1/1976 | Andren | 32/14 |

Primary Examiner—Robert Peshock
Attorney, Agent, or Firm—Stuart S. Bowie

[57] ABSTRACT

A new orthodontic bracket assembly is disclosed together with a method of attachment to a tooth wherein a metal orthodontic bracket with a perforated base is attached to the tooth by means of a photopolymerizable adhesive applied to the area to which the bracket is to be affixed. Subsequent exposure of the adhesive, including particularly portions of adhesive extending through the perforations in the bracket base, to electromagnetic energy of predetermined wave lengths and intensity sufficient to polymerize the adhesive thereby affixes the bracket to the tooth.

4 Claims, 3 Drawing Figures

ORTHODONTIC BRACKET ASSEMBLY AND METHOD FOR ATTACHMENT

The present invention relates to an improved orthodontic bracket assembly and a method for applying the assembly to teeth.

In the past, various difficulties have been encountered in connection with the orthodontic necessity to apply corrective appliances to human teeth pursuant to which certain teeth are displaced to a position of better alignment, and/or occlusion.

One primary need in orthodontic corrections is the maintenance or relatively high tensile forces on the teeth particularly in cases where substantial displacements are required.

In the past, the chief method of applying high tensile forces to the teeth has been to use a series of attachment bands. These bands, which encircle the individual teeth, in general have enabled orthodontists to apply so-called heavy wire tension required for particular corrective treatments. However, the bands have well known deficiencies including difficulty in initial installation thereof and the accompanying pain, which pain often continues to a degree during the entire period of treatment. In addition, the band tends to collect food particles and therefore becomes a potential source of infection and not infrequently decalcification or caries occur in areas covered by or adjacent the bands.

It has been proposed in the past to utilize brackets, i.e., wire guiding and wire anchoring means which do not encircle individual teeth. However, the metal brackets which have been used are difficult to apply since the cold curing cement used with them to affix the brackets to the teeth does not adhere well to the brackets. In practice, this inadequate adhesion has resulted in strictly limited use of metal brackets, where comparatively low forces could be utilized.

It has also been proposed to utilize transparent plastic brackets which do not encircle individual teeth. For example, in my U.S. Pat. No. 3,629,187, granted Dec. 21, 1971, on an application filed June 25, 1969, and U.S. Pat. No. 3,745,653, granted July 17, 1973, upon an application filed Dec. 6, 1971, I disclosed dental materials which were especially suitable for use in cementing transparent plastic brackets to teeth. However, plastic brackets have a limited utility because they are not strong enough to withstand the stresses associated with heavy wire orthodontic corrective treatments over an extended period of time.

In developing the present invention, therefore, I was seeking to provide a means whereby a metal bracket, suitable for heavy wire techniques, could be affixed to teeth speedily at maximum convenience to the orthodontist. In such a fashion, the orthodontist would be able to control the working time of the material by curing the adhesive exactly when conditions were right. At the same time, a stress resistant device would be provided suitable for the heavy wire techniques which are required for major orthodontic treatment. The provision of such an assembly and the method for carrying it out are, therefore, primary objects of the present invention.

THE DRAWINGS

DESCRIPTION OF THE PREFERRED EMBODIMENT

Figure 1:
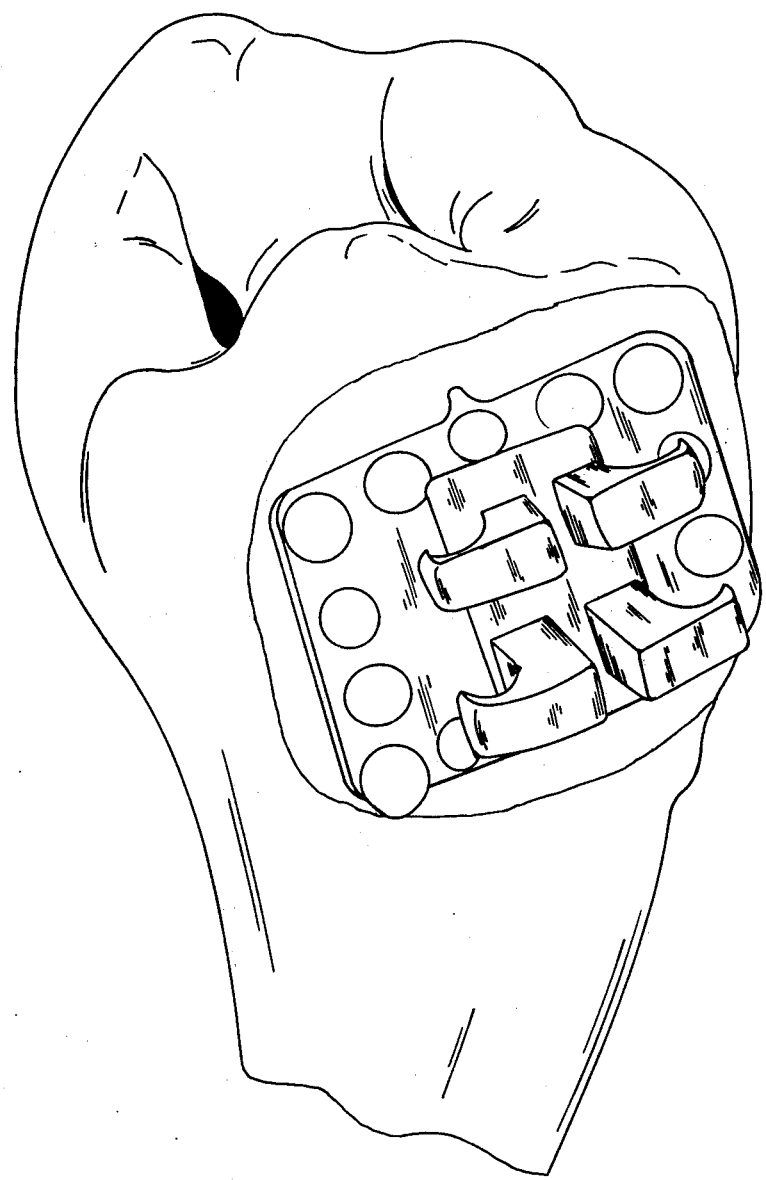
FIG. 1 is a pictoral representation of a preferred embodiment of the orthodontic appliance assembly of the present invention affixed to a tooth.

FIG. 1 is a pictoral representation of a tooth 31 hereinafter for convenience the "anchor" tooth to which the orthodontic bracket assembly 10 of the present invention has been affixed.

Figure 3:
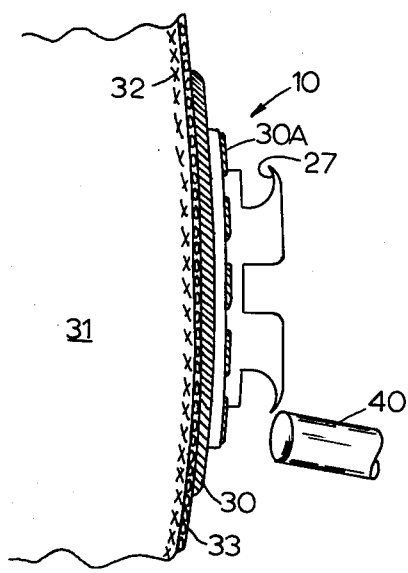
FIG. 3 is an elevational view of the appliance shown in FIG. 1.
Figure 2:
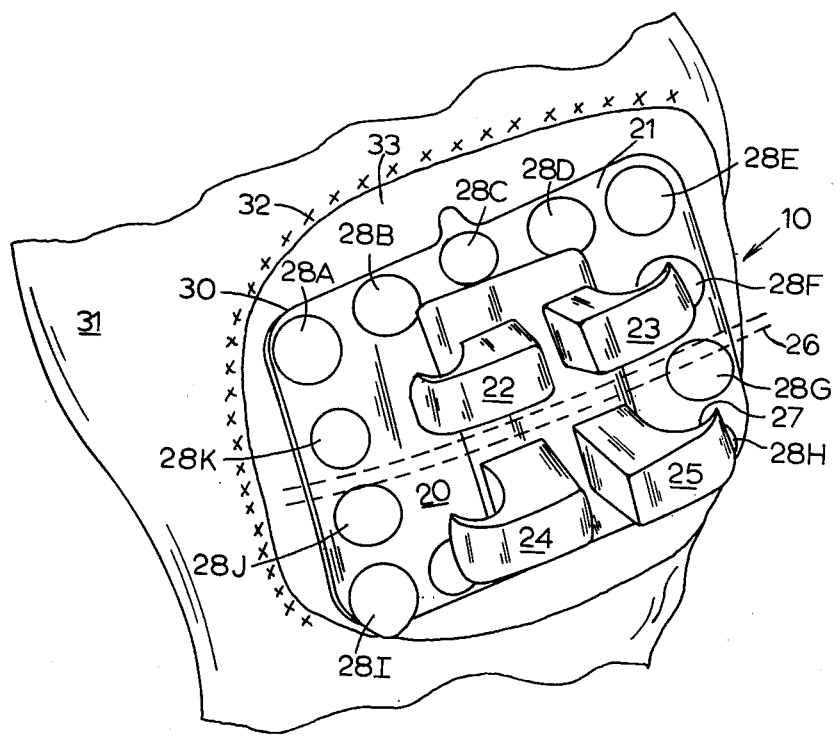
FIG. 2 is a perspective view of the appliance shown in FIG. 1.

FIGS. 2 and 3 indicate the various elements of the assembly shown in FIG. 1. Thus, there is a metal bracket 20 having a base 21 and upstanding posts or guides 22–25. The posts 22–25 are spaced apart to form a channel for wire 26 or similar restraining means which the orthodontist applies for corrective purposes.

The posts 22–25 include a top flange, such as flange 27 shown in connection with post 25, which prevents wire secured around the base of the post from slipping off. Thus, the posts 22–25 are also useful as anchors for the orthodontic wire.

The base 21 of the bracket 20 is perforated. In the present embodiment, the perforations comprise holes 28A–28K but other arrangements, including a mesh configuration, come within the meaning of a "perforated base" as that term is used herein.

The bracket 10 is affixed to the anchor tooth 31 preferably by a photopolymerizable adhesive 30. Prior to such application, the anchor tooth 31 should be cleaned by standard means. The tooth 31 then is preferably etched or conditioned, for example, by application of "Nuva-System" tooth conditioner sold by The L. D. Caulk Company, Division of Dentsply International Inc., (50% phosphoric acid buffered with 7% zinc oxide) with small cotton pledgets using gentle rotary motion for about one minute. The surface is then washed with water and dried by a gentle stream of warm air. This procedure produces an etched area, indicated at 32, over which the bracket 10 is to be placed.

The next step is the application preferably of a sealant 33, such as the polymeric material sold under the trademark "NUVA-SEAL" by The L. D. Caulk Company, Division of Dentsply International Inc., which material can be immediately polymerized by application of ultraviolet light for 30 seconds.

Up to this point, the procedure employed relating to tooth preparation is essentially known. My U.S. Pat. No. 3,709,866, granted Jan. 9, 1973, discloses a variety of photopolymerizable compositions which may be used for sealant purposes. Similar useful materials are also referred to in my U.S. Pat. No. 3,629,187.

However, as far as is known, the present invention is the first successful system whereby a so-called heavy wire metal bracket can be utilized for orthodontic purposes utilizing a cold cured or photopolymerized adhesive. This is made possible by a combination of features of the present invention. In particular, after the sealant 33 is applied, a photopolymerizable adhesive paste 30 is then applied to the rear surface of the base 21 of the bracket 20, and/or to the area covered by the sealent 33. The bracket 20 is then placed against the tooth area covered by the sealant 33 in the position desired by the orthodontist. Pressure is applied against the bracket 20 so that nodules of adhesive 30a are extruded through the perforations 28A–28K of the base 21 of brackets 20. For convenience, these nodules of adhesive 30a are sometimes referred to herein as "rivets" and their tops as "rivet heads".

The adhesive 30 does not polymerize until it is exposed to a suitable source of electromagnetic energy. In the present embodiment, I prefer to use a suitable source of ultraviolet radiation 40. More particularly, a 90 second application using a "Nuva-Lite" ultraviolet activator light produces a strong bond which is secure for practical purposes as soon as the light application is terminated, when "Nuva-Tach" adhesive is used. The "Nuva-Tach" adhesive comprises the following ingredients:

| PASTE | |
|---|---|
| Isopropylidene bis (phenoxy propoxy urethano propane methacrylate) Monomer (containing 250 ppm butylated hydroxy toluene) | 20% by weight |
| Alumina (Average size 1 micron diameter) | 0.6% by weight |
| Lithium aluminum silicate (Average size 15 micron diameter) | 79.4% by weight |
| INITIATOR | |
| Benzoyl peroxide | 3% by weight |
| Benzoin methyl ether | 25% by weight |
| Dibutyl sebacate | 72% by weight or balance |

It will be evident to others in the art that there are other types of photopolymerizable compositions which may be employed for purposes of the adhesive 30 in the present invention. A comprehensive study of photopolymerization may be found in Vol. 68, No. 2 of "Chemical Reviews" of Mar. 25, 1968 beginning at page 125. In addition, the general technique described herein above is discussed in an article entitled "Current Adhesives for Indirect Bonding" which appeared in the Jan. 1974 issue of the *American Journal of Orthodontics* by Silverman and Cohen.

As shown in FIG. 1 of the drawings, the rivet heads 30a undergo flow prior to polymerization so that their cross-section is greater than the diameter of the holes or perforations 28A–28K through which they extrude, thereby locking the bracket 2 to the tooth 31. In practice, the orthodontist can place as many brackets 20 on the teeth as necessary and desirable under the circumstances, and he can accomplish the placement within a relatively short period of time. Furthermore, as described, the use of ultraviolet light, preferably in the wavelength range of approximately 3660 Angstroms for about 90 seconds, produces a polymerization reaction within the adhesive 30 which essentially cures for practical purposes as soon as the ultraviolet light application is finished. In this fashion, the brackets 20 can be placed in exactly the position desired by the orthodontist and the "cementing" thereof to the teeth can be accomplished as the dentist is holding the bracket in place within a relatively few seconds.

It can be observed that this particular technique of using photo-initiated polymerization previously has never been used in the fashion herein described. To the extent that photopolymerization has been disclosed in the past, as in my U.S. Pat. Nos. 3,629,187 and 3,709,866 and 3,745,653, such suggestions have been criticized by certain manufacturers. Moreover, previous efforts have been expressly limited to transparent brackets because up to the present invention, it was not understood how an opaque bracket, such as a metal bracket, could be successfully affixed to a tooth by photopolymerization.

After the brackets 20 are applied to teeth 31, any excess adhesive material is cleaned from the bracket channels and a wire, such as the wire 26, is applied under the proper heavy tension to initate the orthodontic correction.

As noted in the Silverman and Cohen article in the *American Journal of Orthodontics* previously referred to, placement of unbanded metal brackets directly on teeth has probably been the dream of all orthodontists. With the present invention, that dream has been realized. The Silverman and Cohen article may be referred to by those interested in certain further indirect techniques of pre-positioning brackets for use in setting up the case.

The metal brackets of the present invention provide, in combination with the photopolymerizable adhesive used, an exceptionally high bond strength, of the order of 1200–1550 psi (dependent upon bracket size and type), which is very suitable for heavy wiring techniques. This compares with plastic brackets which have a bond strength of the order of 900–1100 psi (dependent upon bracket size and type). However, the plastic brackets fail before the cementation bond when photopolymerization adhesives are utilized. Brackets of such strength are not suitable for heavy wiring techniques and are limited to so-called light wire techniques which are of limited application. However, it is believed that the present invention is the first practical method of attaching metal orthodontic brackets and certainly is the first practical method of attaching metal orthodontic brackets in which the adhesive is a photopolymerizable composition. While, as indicated, there are other prior art techniques whereby metal brackets theoretically could be affixed to teeth (thermal setting and chemical curing for example), such techniques are not practical because they do not give the orthodontist the complete control over timing which is so important in order to minimize working difficulties and be able to correctly position each bracket.

The foregoing description illustrates preferred embodiments of my invention. However, the concepts employed may, based upon such description, be employed in other embodiments without departing from the scope of the invention. Accordingly, the following claims are intended to protect the invention broadly, as well as in the specific forms shown herein.

I claim:

1. A method of constructing an orthodontic appliance assembly comprising the steps of
   A. Applying a photopolymerizable adhesive to an anchor tooth;
   B. Placing a metal bracket including a base having a front and a rear surface with holes extending therethrough against the anchor tooth so that the rear surface contacts said adhesive with sufficient pressure to cause said adhesive to extrude through the holes and to flow on the front surface of the base to form heads having greater cross-sections than the diameters of the holes, and
   C. Applying a source of ultraviolet radiation energy to the adhesive heads extruded through the holes to polymerize the adhesive, whereby the bracket is locked to the anchor tooth.

2. A method of constructing an orthodontic appliance assembly according to the invention of claim 1 wherein the anchor tooth is subjected to a conditioner and coated with a sealant prior to application of the adhesive thereto.

3. A method of affixing a perforated metal orthodontic bracket with a base having holes therethrough to a tooth comprising the steps of
- A. contacting the tooth and the base of the bracket with a photopolymerizable adhesive therebetween,
- B. applying sufficient pressure to the bracket to force at least part of the adhesive through the holes in the base of said bracket to form heads having a cross-section greater than the diameter of the holes, and then
- c. photopolymerizing said adhesive by the application of electromagnetic rediation to said heads to form a mechanical bond between said adhesive and said metal bracket.

4. An orthodontic heavy wire appliance assembly for correcting a dental misconfiguration in a set of teeth comprising a series of opaque metal brackets each affixed to an anchor tooth and heavy wire extending between said brackets, wherein
- a. each bracket includes a metal base having holes therein, said base being non-circumferential of the anchor tooth to which it is attached, and
- b. each bracket is affixed at a bond strength at least about 1200 p.s.i. to its anchor tooth by means of rivets extending thrhough the holes in the base thereof and secured to the tooth by a bonding agent, said rivets having heads on the opposite side of the base, said heads having a cross-section greater than the diameter of the holes through which they extend, and
- c. wherein said bonding agent is a photopolymerizable adhesive comprising particulate lithium aluminum silicate and alumina, together with a sufficient quantity of isopropylidene bis (Penoxy propoxy urethane propane methacrylate) monomer to form a past which when combined with a mixture of benzoin methyl ether, benzoyl peroxide and dibutyl sebacate forms an adhesive composition polymerizable by the application of ultraviolet electromagnetic radiation.

* * * * *